United States Patent
Dimatteo et al.

(10) Patent No.: US 11,484,682 B2
(45) Date of Patent: Nov. 1, 2022

(54) HUMIDIFIER WITH INGRESS PROTECTION FOR USE IN CPAP THERAPY

(71) Applicant: KONINKLIJKE PHILIPS N.V., Eindhoven (NL)

(72) Inventors: Mark William Dimatteo, Irwin, PA (US); Mark Wayne Barclay, Saxonburg, PA (US); Michael Eugene Mort, Somerset, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 354 days.

(21) Appl. No.: 16/582,218

(22) Filed: Sep. 25, 2019

(65) Prior Publication Data

US 2020/0101258 A1    Apr. 2, 2020

Related U.S. Application Data

(60) Provisional application No. 62/738,376, filed on Sep. 28, 2018.

(51) Int. Cl.
*A61M 16/16*    (2006.01)

(52) U.S. Cl.
CPC .......... *A61M 16/162* (2013.01); *A61M 16/16* (2013.01)

(58) Field of Classification Search
CPC ........ A61M 16/16; A61M 16/162; F24F 6/02; F24F 6/025; F24F 6/04; F24F 6/043; F24F 6/06; F24F 6/08; F24F 6/10; F24F 6/105; F24F 2006/008
See application file for complete search history.

(56) References Cited

U.S. PATENT DOCUMENTS

| | | | |
|---|---|---|---|
| 3,667,463 A * | 6/1972 | Barnes | A61M 16/16 128/203.16 |
| 5,511,539 A | 4/1996 | Lien | |
| 8,757,154 B2 * | 6/2014 | Schuller | A61M 16/107 128/205.12 |
| 10,322,257 B2 | 6/2019 | Dimatteo | |
| 2007/0035044 A1 * | 2/2007 | Chiu | F24F 6/02 261/81 |

(Continued)

FOREIGN PATENT DOCUMENTS

| | | | |
|---|---|---|---|
| DE | 10016005 A1 * | 12/2001 | ............ A61M 16/16 |
| DE | 102004052054 A1 * | 4/2006 | ........ A61M 16/1075 |

(Continued)

*Primary Examiner* — Kathryn E Ditmer

(57) ABSTRACT

An apparatus includes a housing having a gas flow generator for generating a flow of breathing gas and a humidifier disposed therein having a chamber for housing a volume of water. The chamber has a top opening for providing the volume of water therein. The apparatus further includes a lid coupled to the housing that is movable between a first position wherein the lid covers the top opening and a second position wherein the lid does not cover the top opening. The apparatus also includes a passage which extends from a first end positioned and structured to receive the flow of breathing gas from the gas flow generator to an opposite second end positioned on the lid and structured to expel the flow of breathing gas into the chamber. An outlet for conveying the flow of breathing gas from the chamber out of the housing is positioned on the housing.

20 Claims, 6 Drawing Sheets

(56) References Cited

U.S. PATENT DOCUMENTS

2009/0301482 A1* 12/2009 Burton .............. A61M 16/1075
128/203.12
2013/0008440 A1   1/2013 Maurer
2013/0247911 A1   9/2013 Martin
2018/0015310 A1*  1/2018 Choi ........................ F24F 8/10

FOREIGN PATENT DOCUMENTS

JP    2005287596 A  * 10/2005  ............ A61M 16/16
WO      02066106 A1    8/2002
WO    2014138804 A1    9/2014

* cited by examiner

HUMIDIFIER WITH INGRESS PROTECTION FOR USE IN CPAP THERAPY

This application claims the benefit of U.S. Provisional Application No. 62/738,376, filed Sep. 28, 2018. This application is hereby incorporated by reference herein.

BACKGROUND OF THE INVENTION

1. Field of the Invention

The present invention pertains to humidifiers for use in airway pressure support systems for delivering a flow of a humidified gas to the airway of a patient and, more particularly to arrangements for preventing the passage of water outward from the inlet of such humidifiers.

2. Description of the Related Art

Many individuals suffer from disordered breathing during sleep. Sleep apnea is a common example of such sleep disordered breathing suffered by millions of people throughout the world. One type of sleep apnea is obstructive sleep apnea (OSA), which is a condition in which sleep is repeatedly interrupted by an inability to breathe due to an obstruction of the airway; typically the upper airway or pharyngeal area. Obstruction of the airway is generally believed to be due, at least in part, to a general relaxation of the muscles which stabilize the upper airway segment, thereby allowing the tissues to collapse the airway. Another type of sleep apnea syndrome is a central apnea, which is a cessation of respiration due to the absence of respiratory signals from the brain's respiratory center. An apnea condition, whether obstructive, central, or mixed, which is a combination of obstructive and central, is defined as the complete or near cessation of breathing, for example a 90% or greater reduction in peak respiratory air-flow.

Those afflicted with sleep apnea experience sleep fragmentation and complete or nearly complete cessation of ventilation intermittently during sleep with potentially severe degrees of oxyhemoglobin desaturation. These symptoms may be translated clinically into extreme daytime sleepiness, cardiac arrhythmias, pulmonary-artery hypertension, congestive heart failure and/or cognitive dysfunction. Other consequences of sleep apnea include right ventricular dysfunction, carbon dioxide retention during wakefulness, as well as during sleep, and continuous reduced arterial oxygen tension. Sleep apnea sufferers may be at risk for excessive mortality from these factors as well as by an elevated risk for accidents while driving and/or operating potentially dangerous equipment.

Even if a patient does not suffer from a complete or nearly complete obstruction of the airway, it is also known that adverse effects, such as arousals from sleep, can occur where there is only a partial obstruction of the airway. Partial obstruction of the airway typically results in shallow breathing referred to as a hypopnea. A hypopnea is typically defined as a 50% or greater reduction in the peak respiratory air-flow. Other types of sleep disordered breathing include, without limitation, upper airway resistance syndrome (UARS) and vibration of the airway, such as vibration of the pharyngeal wall, commonly referred to as snoring.

It is well known to treat sleep disordered breathing by applying a continuous positive air pressure (CPAP) to the patient's airway. This positive pressure effectively "splints" the airway, thereby maintaining an open passage to the lungs. It is also known to provide a positive pressure therapy in which the pressure of gas delivered to the patient varies with the patient's breathing cycle, or varies with the patient's breathing effort, to increase the comfort to the patient. This pressure support technique is referred to as bi-level pressure support, in which the inspiratory positive airway pressure (IPAP) delivered to the patient is higher than the expiratory positive airway pressure (EPAP). It is further known to provide a positive pressure therapy in which the pressure is automatically adjusted based on the detected conditions of the patient, such as whether the patient is experiencing an apnea and/or hypopnea. This pressure support technique is referred to as an auto-titration type of pressure support, because the pressure support device seeks to provide a pressure to the patient that is only as high as necessary to treat the disordered breathing.

Pressure support therapies as just described involve the placement of a patient interface device including a mask component having a soft, flexible sealing cushion on the face of the patient. The mask component may be, without limitation, a nasal mask that covers the patient's nose, a nasal/oral mask that covers the patient's nose and mouth, or a full face mask that covers the patient's face. Such patient interface devices may also employ other patient contacting components, such as forehead supports, cheek pads and chin pads. The patient interface device is typically secured to the patient's head by a headgear component. The patient interface device is connected to a gas delivery tube or conduit and interfaces the pressure support device with the airway of the patient, so that a flow of breathing gas can be delivered from the pressure/flow generating device to the airway of the patient.

Humidifiers are frequently provided between or integral with a PAP machine and the user interface in order to humidify the otherwise relatively-dry compressed air generated by the PAP machine. The most conventional type of humidification used in homecare ventilation is a passover arrangement. In such arrangement, air from the CPAP machine flows into a water chamber and over an area of water W before exiting the humidifier and passing on to the patient. This carries the moisture via a patient circuit (tubing+mask) to the patient. The water can be at room temperature or at an elevated temperature. The elevated temperate approach is more popular because it delivers more water in the air due to the fact that it is heated. The water for this type of humidifier is commonly heated using a resistive heater and has multiple set points for comfort.

Humidifiers are typically an integral part of the ventilator (i.e. CPAP) and are therefore most likely to be directly connected to the flow generator. Within the flow generator there are sensitive parts and assemblies that can easily be damaged by water ingress. These include a motor/blower assembly, pressure and flow sensors and other electronic devices not able to withstand water without damage or diminished performance. During use, the patient must be able to interact with the water chamber that contains the water that will supply humidity to the airway during therapy. During this interaction, and depending on the form factor of the humidifier, the water contained in the chamber can enter the flow generator unintentionally (e.g., due to mis-pouring, over-filling, etc.). Accordingly, a need exists for improved arrangements which minimize and preferably eliminate such occurrences of water ingress to the flow generator.

SUMMARY OF THE INVENTION

Embodiments of the present invention minimize or eliminate the potential for such water ingress to the flow generator while allowing for the water chamber to be filled while the water chamber is still installed in the humidifier and attached to the flow generator. Embodiments of the invention routes the airway path generally through a pivoting point of the water chamber lid which when raised, positions the outlet from the above the water chamber and therefore eliminates the possibility of water entering the flow generator.

As one aspect of the disclosed concept, an apparatus for providing a flow of breathing gas for a patient is provided. The apparatus comprises: a housing; a gas flow generator disposed in the housing, the gas flow generator structured to generate the flow of breathing gas; a humidifier disposed in the housing, the humidifier having a water chamber structured to house a volume of water therein, the water chamber having a top opening for providing the volume of water in the chamber; a lid coupled to the housing such that the lid is movable between a first position wherein the lid covers the top opening of the water chamber and a second position wherein the lid does not cover the top opening of the water chamber; a passage which extends from a first end positioned and structured to receive the flow of breathing gas from the gas flow generator to an opposite second end positioned on the lid and structured to expel the flow of breathing gas into the chamber; and an outlet positioned on the housing, the outlet being structured to convey the flow of breathing gas from the chamber out of the housing.

The lid may be rotatably coupled to the housing via a hinge arrangement such that the lid is rotatable about a rotational axis.

A portion of the passage may be defined by the hinge arrangement.

The hinge arrangement may comprise a generally cylindrical portion disposed about the rotational axis; the portion may comprise a hollow defined in the cylindrical portion.

The hollow may extend from an inlet which is positioned to initially receive the flow of breathing gas entering the hollow; and the inlet may be disposed on an axial face of the cylindrical portion.

The hollow may extend from an inlet which is positioned to initially receive the flow of breathing gas entering the hollow; and wherein the inlet is disposed on a circumferential face of the cylindrical portion.

When the lid is disposed in the first position the inlet may be positioned to receive the flow of breathing gas; and when the lid is disposed in the second position the inlet may be positioned to not receive the flow of breathing gas.

The cylindrical portion may be fixedly coupled to the lid.

The hollow may extend from an inlet to a side outlet; and the portion may further comprise a generally straight section which extends from the side outlet to the opposite second end of passage.

The lid may comprise an inner lid and the apparatus may further comprise an outer lid coupled to the housing such that the outer lid is movable between a first position wherein the outer lid covers the inner lid and a second position wherein the outer lid does not cover the inner lid.

The housing may comprise a first housing and a second housing selectively coupled to the first housing; and the gas flow generator may be disposed in the first housing and the humidifier may be disposed in the second housing.

As another aspect of the disclosed concept, an airway pressure support system use in providing a flow of breathing gas to the airway of a patient is provided. The system comprises an apparatus for providing a flow of breathing gas for a patient, the apparatus comprising: a housing; a gas flow generator disposed in the housing, the gas flow generator structured to generate the flow of breathing gas; a humidifier disposed in the housing, the humidifier having a water chamber structured to house a volume of water therein, the water chamber having a top opening for providing the volume of water in the chamber; a lid coupled to the housing such that the lid is movable between a first position wherein the lid covers the top opening of the water chamber and a second position wherein the lid does not cover the top opening of the water chamber; a passage which extends from a first end positioned and structured to receive the flow of breathing gas from the gas flow generator to an opposite second end positioned on the lid and structured to expel the flow of breathing gas into the chamber; and an outlet positioned on the housing, the outlet being structured to convey the flow of breathing gas from the chamber out of the housing. The system further comprises: a delivery conduit having a first end coupled to the outlet of the apparatus and an opposite second end, the conduit being structured to convey the flow of breathing gas from the first end to the second end; and a patient interface device coupled to the second end of the conduit for providing the flow of treatment gas to an airway of the patient.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

DETAILED DESCRIPTION OF EXEMPLARY EMBODIMENTS

Figure 1:
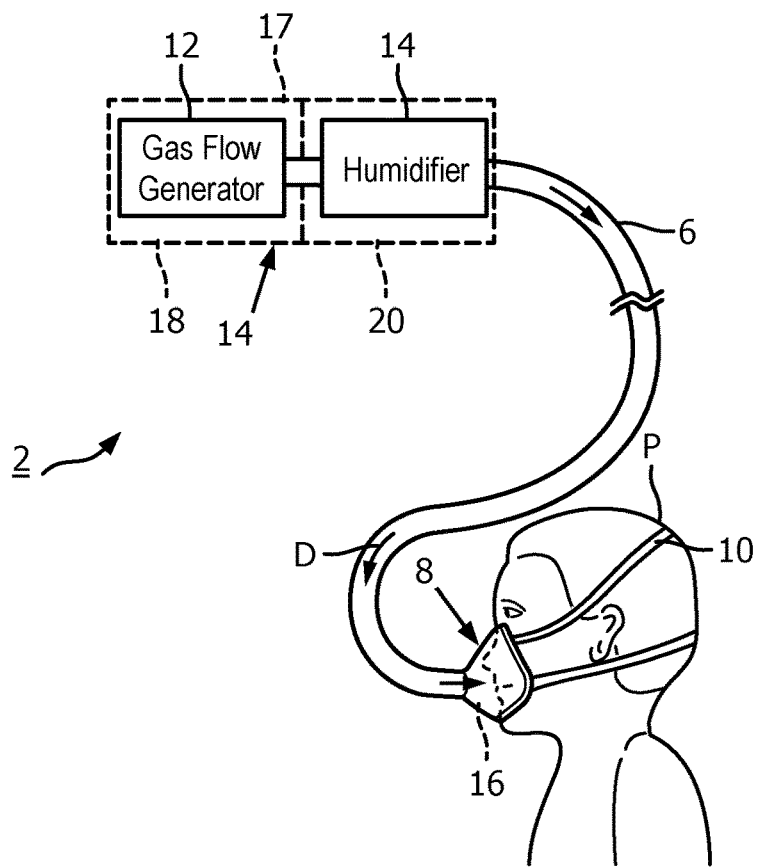
FIG. 1 is a schematic diagram of an airway pressure support system according to one particular, non-limiting embodiment in which the present invention in its various embodiments may be implemented, shown with a patient interface device thereof disposed on the face of a patient.

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are coupled directly in contact with each other. As used herein, "fixedly coupled" or "fixed" means that two components are coupled so as to move as one while maintaining a constant orientation relative to each other. As used herein, "selectively coupled" means that two elements are coupled in a manner in which the two elements may be readily uncoupled or recoupled.

As used herein, the word "unitary" means a component is created as a single piece or unit. That is, a component that includes pieces that are created separately and then coupled together as a unit is not a "unitary" component or body. As used herein, the statement that two or more parts or components "engage" one another shall mean that the parts exert a force against one another either directly or through one or more intermediate parts or components. As used herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

FIG. 1 is a schematic diagram of an airway pressure support system 2 according to one particular, non-limiting embodiment in which the present invention in its various embodiments may be implemented. Pressure support system 2 includes an apparatus 4 for providing a flow of breathing gas, a delivery conduit 6 for communicating the flow of breathing gas, a patient interface device 8 structured to receive the flow of breathing gas from conduit 6 and engage about an airway of the patient, and a headgear 10 for securing patient interface device 8 to the head of a patient (P).

Apparatus 4 includes a gas flow generator 12 which is structured to generate the flow of breathing gas to be delivered through patient interface device 8 to the airway of patient P. The flow of breathing gas may be heated and/or humidified by a humidifier 14 provided as a portion of apparatus 4. Gas flow generator 12 and humidifier 14 may be: provided in a common or main housing 17, or provided in separate housings 18, 20 which may be selectively coupled and uncoupled with each other via any suitable coupling arrangement.

Gas flow generator 12 may include, without limitation, ventilators, constant pressure support devices (such as a continuous positive airway pressure device, or CPAP device), variable pressure devices (e.g., BiPAP®, Bi-Flex®, or C-Flex™ devices manufactured and distributed by Philips Respironics of Murrysville, Pa.), and auto-titration pressure support devices. Delivery conduit 6 is structured to communicate the flow of breathing gas from apparatus 4 to patient interface device 8. Delivery conduit 6 and patient interface device 8 are often collectively referred to as a patient circuit.

A BiPAP® device is a bi-level device in which the pressure provided to the patient varies with the patient's respiratory cycle, so that a higher pressure is delivered during inspiration than during expiration. An auto-titration pressure support system is a system in which the pressure varies with the condition of the patient, such as whether the patient is snoring or experiencing an apnea or hypopnea. The present invention contemplates that gas flow generator 12 is any conventional system for delivering a flow of gas to an airway of a patient or for elevating a pressure of gas at an airway of the patient, including the pressure support systems summarized above and non-invasive ventilation systems. Although described herein in example embodiments wherein a pressurized flow of gas is utilized, it is to be appreciated that embodiments of the invention as described herein could also be readily employed in other generally non-pressurized applications (e.g., without limitation, in high flow therapy applications).

In the exemplary embodiment shown in FIG. 1, patient interface device 8 includes a patient sealing assembly 16, which in the illustrated embodiment is a full face mask. It is to be appreciated, however, that other types of patient sealing assemblies, such as, without limitation, a nasal/oral mask, a nasal cushion, or any other arrangements which facilitate the delivery of the flow of breathing gas to the airway of a patient may be substituted for patient sealing assembly 16 while remaining within the scope of the present invention. It is also to be appreciated that headgear 10 is provided solely for exemplary purposes and that any suitable headgear arrangement may be employed without varying from the scope of the present invention.

Referring to FIGS. 2-6, various detailed views of an example apparatus 4 in accordance with one example embodiment of the present invention are shown. As previously discussed in regard to the schematic illustration of FIG. 1, apparatus 4 generally includes a gas flow generator 12 (FIGS. 4 and 5) and a humidifier 14 positioned in a main housing 17. Gas flow generator 12 is structured to generate the flow (shown schematically by arrows F) of breathing gas and humidifier 14 is structured to humidify the flow of breathing gas produced by gas flow generator.

Figure 2:
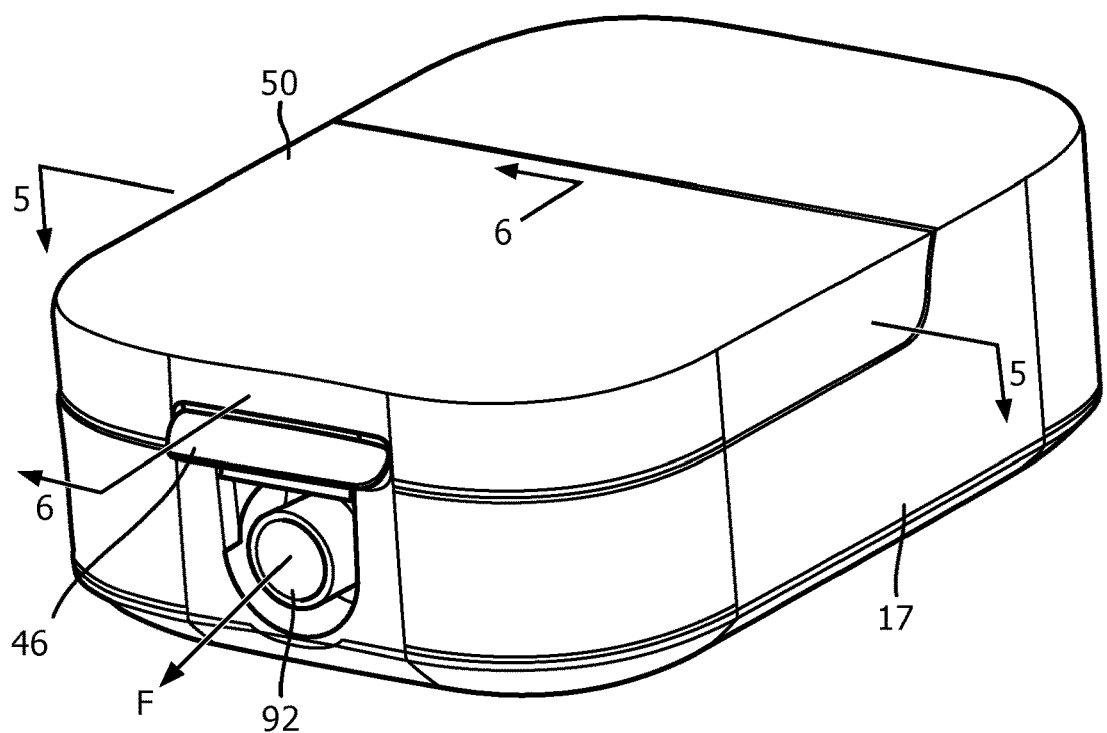
FIG. 2 is an isometric view of an apparatus for humidifying a flow of treatment gas according to one particular, non-limiting embodiment of the present invention.
Figure 3:
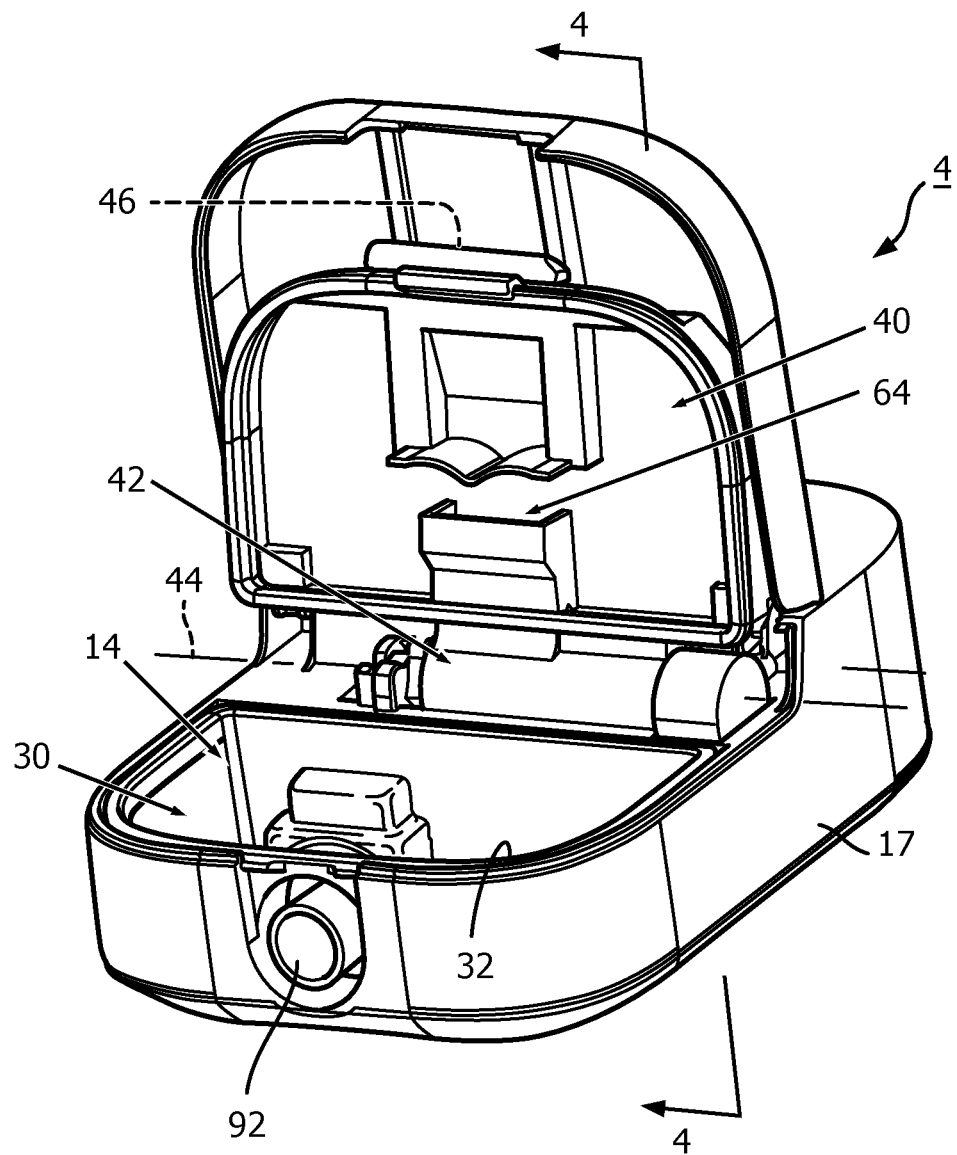
FIG. 3 is an isometric view of the apparatus of FIG. 2, shown with an inner lid and an outer lid disposed in an open position to shoe internal structures.
Figure 4:
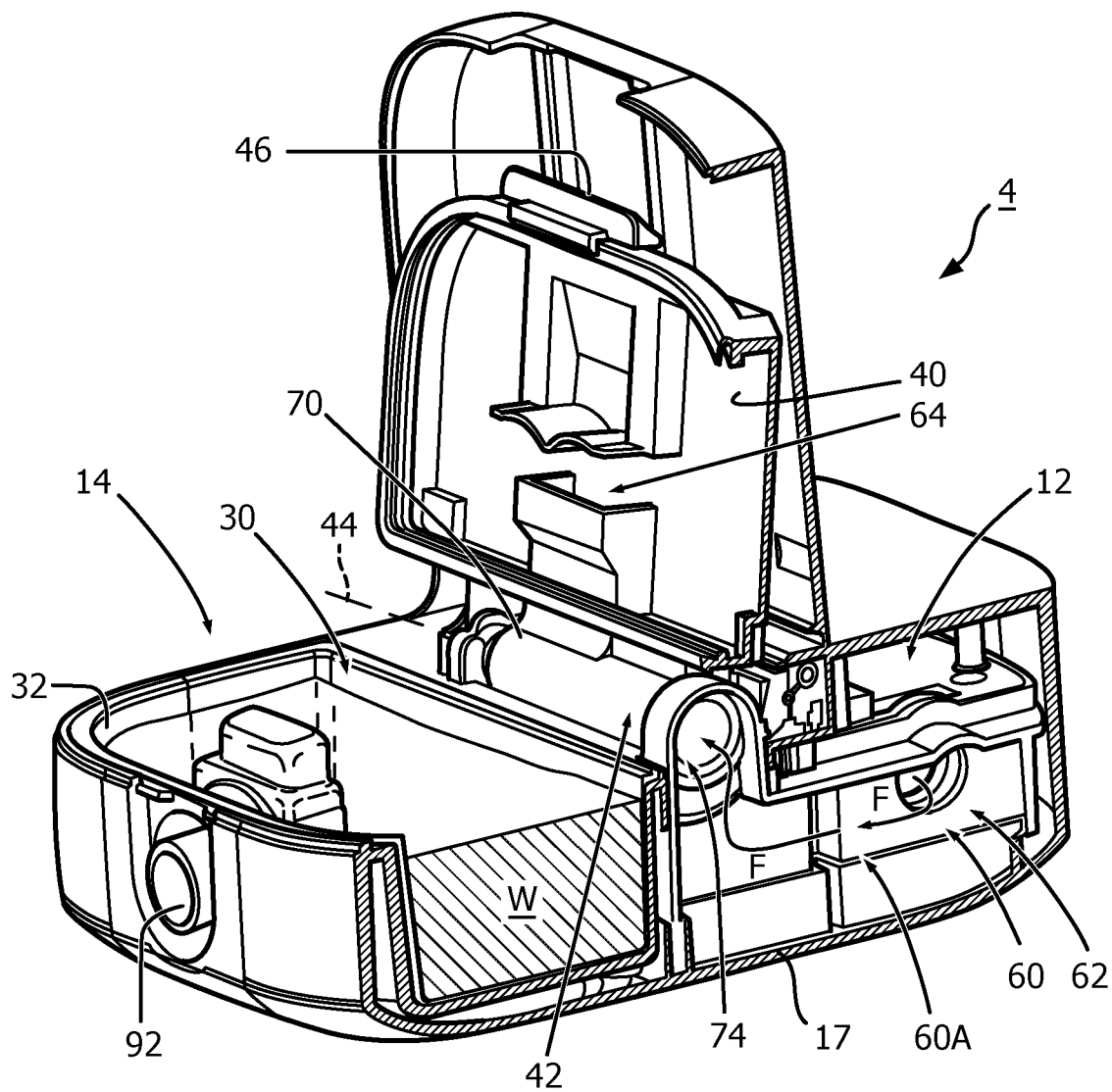
FIG. 4 is a side isometric view of the apparatus of FIG. 2, showing a section view taken generally long line 4-4 of FIG. 3.
Figure 5:
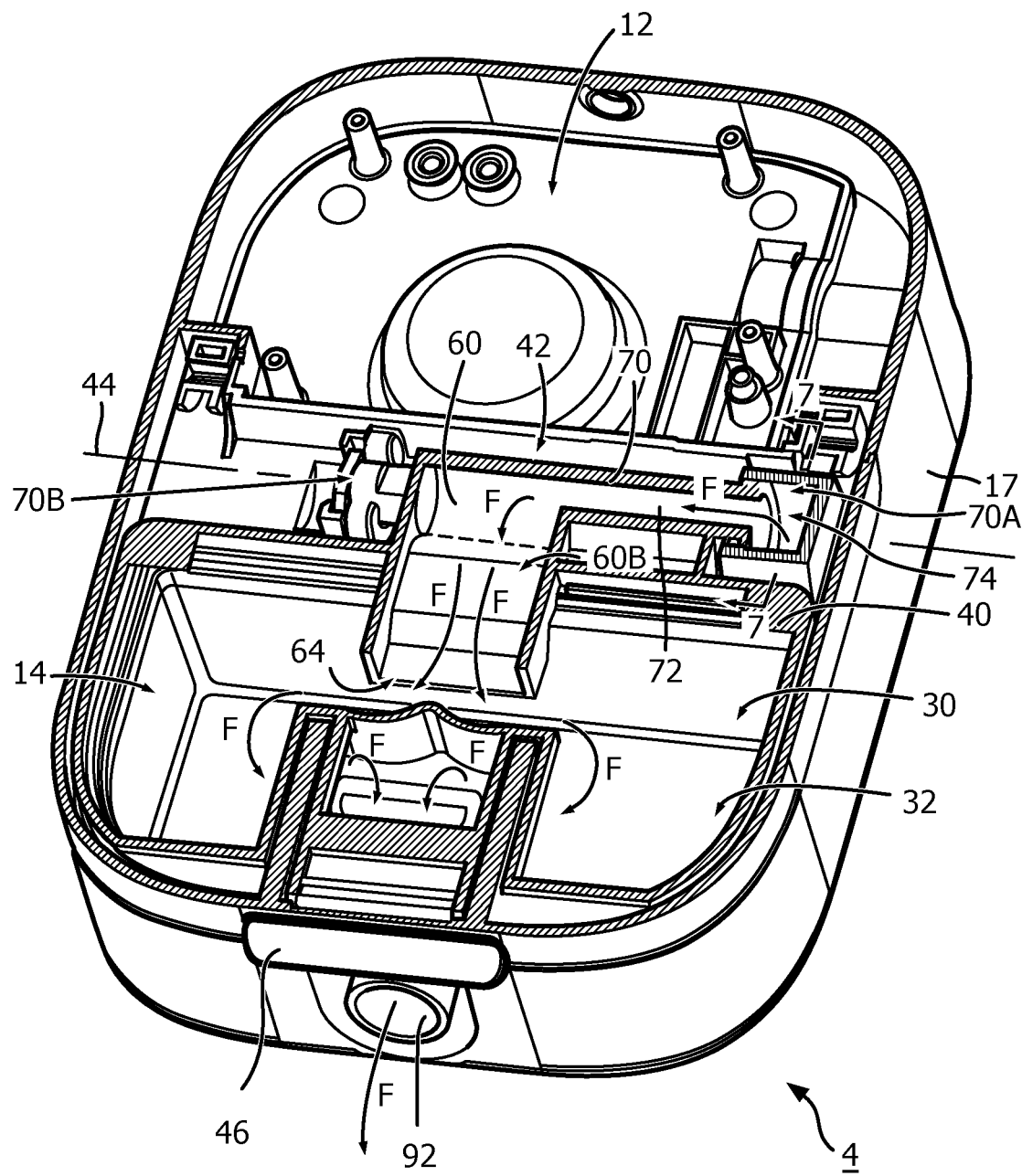
FIG. 5 is a top isometric view of the apparatus of FIG. 2, showing a section view generally along line 5-5 of FIG. 2.
Figure 6:
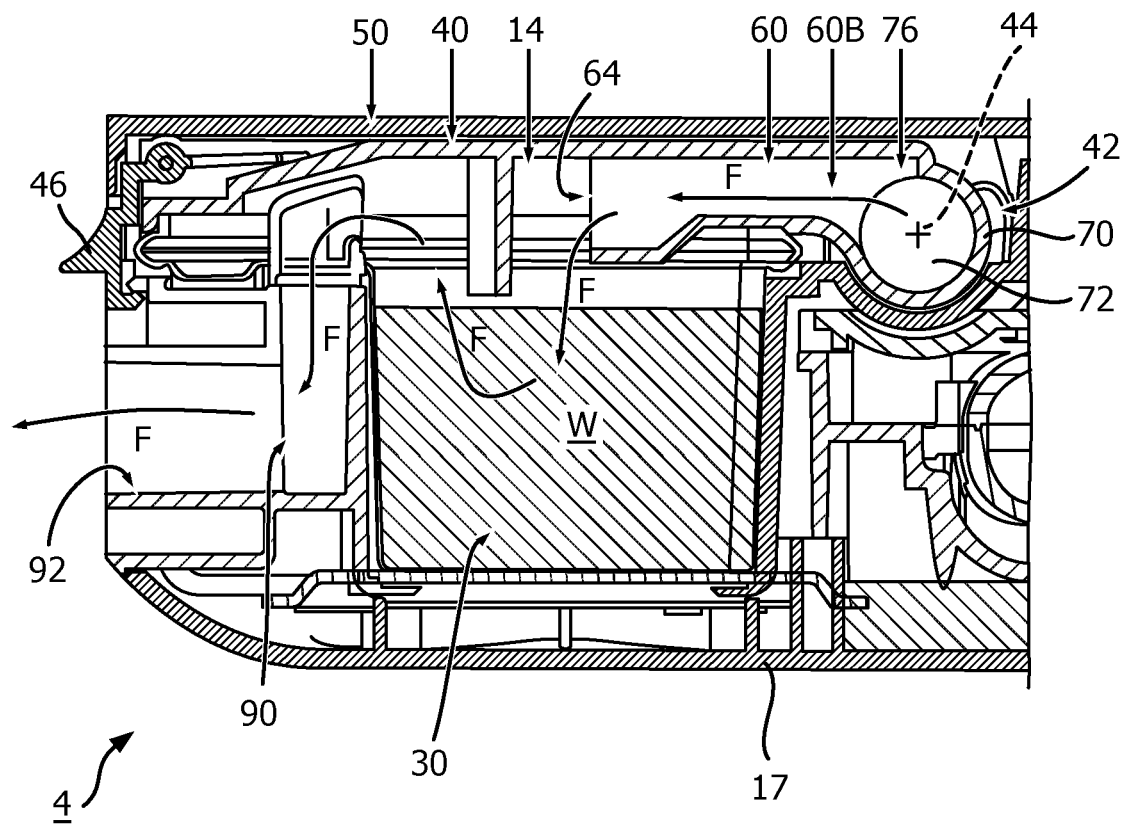
FIG. 6 is a sectional elevation view taken generally along line 6-6 of FIG. 2.

Referring to FIGS. 3-6, humidifier 14 includes a water chamber 30 which is structured to house a volume of water W therein. Water chamber 30 is generally accessible via a top opening 32 via which volume of water W may be provided (e.g., via a water faucet, pitcher, etc.) in chamber 30, as-needed, by a user of apparatus 4. Access to to opening 32 is governed by an inner lid 40 coupled to housing 17, so as to move as movable portion thereof. Accordingly, lid 40 is movable between a first position (FIGS. 1, 5 and 6) wherein inner lid 40 covers top opening 32 of water chamber 30, and a second position (FIGS. 3 and 4) wherein inner lid 40 does not cover top opening 32 of water chamber 30. In the example embodiment, inner lid 40 is rotatably coupled to housing 17 via a hinge arrangement 42 so as to rotate about a rotational axis 44. Inner lid 40 may include a latch mechanism 46 generally opposite the portion thereof which is coupled to housing 17, for use in reliably securing inner lid 40 in the aforementioned first position to housing 17, such as generally shown in FIGS. 2 and 6. In addition to inner lid 40, an outer lid 50 may further be provided which is coupled to housing 17 such that outer lid 50 is movable between a first position (FIGS. 2, 5 and 6) wherein outer lid 50 covers inner lid 40, and a second position (FIGS. 3 and 4) wherein outer lid 50 does not cover inner lid 40. In the example embodiment, outer lid 50 is rotatably coupled to housing 17 so as to rotate about a second rotational axis (not numbered) disposed generally parallel to rotational axis 44.

Referring to FIGS. 4-6, the flow F of breathing gas produced by flow generator 12 is conveyed via a passage 60, which extends from a first end (shown generally at 62 in FIG. 4) which is positioned and structured to receive the flow F of breathing gas from gas flow generator 12, to an opposite second end 64 which is disposed on inner lid 40 and which is positioned and structured to expel the flow F of breathing gas into chamber 30 of humidifier 14. In the illustrated example embodiment, passage 60 generally includes two portions: i) a first portion 60A (FIG. 4) defined generally by housing 17 and internal components (not numbered) of apparatus 4; and ii) a second portion 60B (FIGS. 5 and 6) defined generally by hinge arrangement 42 and inner lid 40.

Figure 7A:
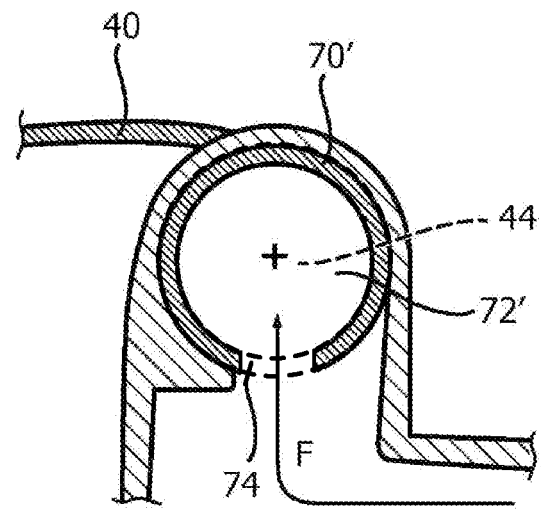
FIGS. 7A and 7B show sectional views, such as would be viewed generally along line 7-7 of FIG. 5 of a portion of a hinge arrangement in accordance with another non-limiting embodiment of the present invention with a portion thereof shown disposed in first and second positionings.
Figure 7B:
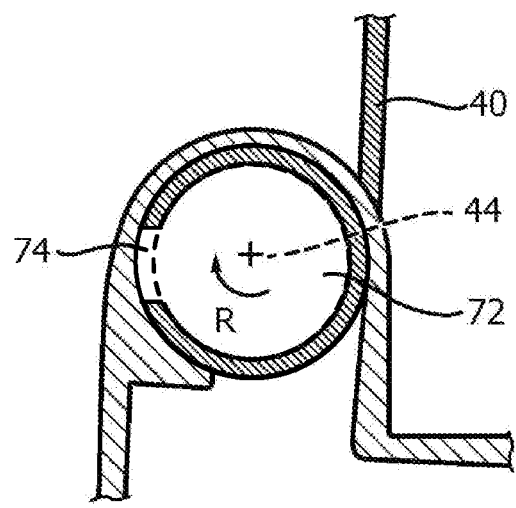

More particularly, as shown in FIGS. 4 and 5, hinge arrangement 42 includes a generally cylindrical portion 70 to which inner lid 40 is fixedly coupled. Cylindrical portion 70 is disposed about rotational axis 44, such that the central longitudinal axis of cylindrical portion 70 coincides with rotational axis 44. Cylindrical portion 70 is coupled at or about opposing ends 70A, 70B to housing 17 such that cylindrical portion 70 (as well as inner lid 40) is rotatable about rotational axis 44. Cylindrical portion 70 includes a hollow 72 defined therein which extends from an inlet 74 disposed at or about first end 70A, toward a second end 70B of cylindrical portion 70, and ends at a side outlet 76 which is disposed generally parallel to rotational axis 44. In the example shown in FIGS. 4 and 5, inlet 74 is defined in an axial face (not numbered) at first end 70A such that the flow F of breathing gas enters hollow 72 generally axially along rotational axis 44. In such arrangement, inlet 74 is always "open", regardless of the rotational positioning of cylindrical portion 70. In contrast, FIGS. 7A and 7B illustrate a sectional view of another example embodiment in which inlet 74 is defined in a circumferential face (not numbered) of cylindrical portion 70' (and the axial face is closed). In such arrangement, when cylindrical portion 70' (as well as inner lid 40) is positioned in a "closed" position, such as shown in FIG. 7A, inlet 74 is positioned to receive the flow F of breathing gas. However, when cylindrical portion 70' (as well as inner lid 40) is positioned in an "open" position (e.g., via rotation of inner lid 40 and cylindrical portion 70' about 90° in the direction R), such as shown in FIG. 7B, inlet 74 is covered, thus preventing passage of fluids (e.g., flow F, water) in either direction through inlet 74. It is to be appreciated that the arrangement of hinge arrangement 42 may be generally reversed (i.e., cylindrical portions 70, 70' fixedly coupled to housing 17 and providing flow to a passage on inner lid 40 via inlet 74) without varying from the scope of the present concept. Additionally, it is to be appreciated that other arrangements which provide for a passage from gas flow generator 12 to an outlet positioned on a portion of inner lid 40 similarly to outlet 64 may be employed without varying from the scope of the present invention.

Referring again to FIGS. 4-6, second portion 60B of passage 60 further includes a generally straight section 80 which extends along an underside (not numbered) inner lid 40 from side outlet 76 of cylindrical portion 70 and terminates at opposite second end 64.

Referring now to FIGS. 5 and 6, after being exposed to (and humidified by) water W in chamber 30, the flow F of breathing gas exits chamber 30 via an exit passage 90 (FIG. 6) which terminates at an outlet 92. Outlet 92 is positioned on an exterior of housing 17 and is structured such that a conduit, such as conduit 6, previously discussed in conjunction with FIG. 1, may be readily coupled thereto for further communicating the now humidified flow F of breathing gas to a patient interface device engaged with an airway of a patient.

From the foregoing, it is to be appreciated that embodiments of the present invention provide arrangements which allow for a water chamber of a humidifier to be filled/refilled while such chamber is installed in a CPAP apparatus with minimal chance of water ingress to the flow generating device.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

What is claimed is:

1. An apparatus for providing a flow of breathing gas for a patient, the apparatus comprising:
    a housing;
    a gas flow generator disposed in the housing, the gas flow generator structured to generate the flow of breathing gas;
    a humidifier disposed in the housing, the humidifier having a water chamber structured to house a volume of water therein, the water chamber having a top opening for providing the volume of water in the chamber;
    a lid coupled to the housing via a coupling arrangement such that the lid is movable between a first position wherein the lid covers the top opening of the water chamber and a second position wherein the lid does not cover the top opening of the water chamber;
    a passage which extends from a first end positioned and structured to receive the flow of breathing gas from the gas flow generator to an opposite second end positioned on the lid and structured to expel the flow of breathing gas into the chamber, wherein a portion of the passage is defined by the coupling arrangement; and
    an outlet positioned on the housing, the outlet being structured to convey the flow of breathing gas from the chamber out of the housing,
    wherein the coupling arrangement comprises a generally cylindrical portion disposed about a rotational axis of the lid relative to the housing; and wherein the portion of the passage comprises a hollow defined in the cylindrical portion.

2. The apparatus of claim 1, wherein the lid comprises an inner lid and wherein the apparatus further comprises an outer lid coupled to the housing, wherein the outer lid is movable between a first position wherein the outer lid covers the inner lid and a second position wherein the outer lid does not cover at least a portion of the inner lid.

3. The apparatus of claim 1, wherein the housing comprises a first housing portion and a second housing portion; and wherein the gas flow generator is disposed in the first housing portion and the humidifier is disposed in the second housing portion.

4. The apparatus of claim 1, wherein the hollow extends from an inlet which is positioned to initially receive the flow of breathing gas entering the hollow; and wherein the inlet is disposed on an axial face of the cylindrical portion.

5. The apparatus of claim 1, wherein the hollow extends from an inlet which is positioned to initially receive the flow of breathing gas entering the hollow; and wherein the inlet is disposed on a circumferential face of the cylindrical portion.

6. The apparatus of claim 5, wherein, when the lid is disposed in the first position, the inlet is positioned to receive the flow of breathing gas; and
wherein, when the lid is disposed in the second position, the inlet is positioned to not receive the flow of breathing gas.

7. The apparatus of claim 1, wherein the cylindrical portion is fixedly coupled to the lid.

8. The apparatus of claim 1, wherein the hollow extends from an inlet to a side outlet; and wherein the portion of the passage further comprises a generally straight section which extends from the side outlet to the opposite second end of the passage.

9. An apparatus for providing a flow of breathing gas for a patient, the apparatus comprising:
a housing;
a gas flow generator disposed in the housing, the gas flow generator structured to generate the flow of breathing gas;
a humidifier disposed in the housing, the humidifier having a water chamber structured to house a volume of water therein, the water chamber having a top opening for providing the volume of water in the chamber;
a lid coupled to the housing such that the lid is movable between a first position wherein the lid covers the top opening of the water chamber and a second position wherein the lid does not cover the top opening of the water chamber;
a passage which extends from a first end positioned and structured to receive the flow of breathing gas from the gas flow generator to an opposite second end positioned on the lid and structured to expel the flow of breathing gas into the chamber; and
an outlet positioned on the housing, the outlet being structured to convey the flow of breathing gas from the chamber out of the housing,
wherein the lid is rotatably coupled to the housing via a hinge arrangement such that the lid is rotatable about a rotational axis, and wherein a portion of the passage is defined by the hinge arrangement.

10. The apparatus of claim 9, wherein the hinge arrangement comprises a generally cylindrical portion disposed about the rotational axis; and wherein the portion of the passage comprises a hollow defined in the cylindrical portion.

11. The apparatus of claim 10, wherein the hollow extends from an inlet which is positioned to initially receive the flow of breathing gas entering the hollow; and wherein the inlet is disposed on an axial face of the cylindrical portion.

12. The apparatus of claim 10, wherein the hollow extends from an inlet which is positioned to initially receive the flow of breathing gas entering the hollow; and wherein the inlet is disposed on a circumferential face of the cylindrical portion.

13. The apparatus of claim 12, wherein, when the lid is disposed in the first position, the inlet is positioned to receive the flow of breathing gas; and wherein, when the lid is disposed in the second position, the inlet is positioned to not receive the flow of breathing gas.

14. The apparatus of claim 10, wherein the cylindrical portion is fixedly coupled to the lid.

15. The apparatus of claim 10, wherein the hollow extends from an inlet to a side outlet; and wherein the portion of the passage further comprises a generally straight section which extends from the side outlet to the opposite second end of the passage.

16. The apparatus of claim 9, wherein the lid comprises an inner lid and wherein the apparatus further comprises an outer lid coupled to the housing, wherein the outer lid is movable between a first position wherein the outer lid covers the inner lid and a second position wherein the outer lid does not cover at least a portion of the inner lid.

17. An airway pressure support system for providing a flow of breathing gas to an airway of a patient, the system comprising:
an apparatus for providing a flow of breathing gas for a patient, the apparatus comprising:
a housing;
a gas flow generator disposed in the housing, the gas flow generator structured to generate the flow of breathing gas;
a humidifier disposed in the housing, the humidifier having a water chamber structured to house a volume of water therein, the water chamber having a top opening for providing the volume of water in the chamber;
a lid coupled to the housing via a coupling arrangement such that the lid is movable between a first position wherein the lid covers the top opening of the water chamber and a second position wherein the lid does not cover the top opening of the water chamber;
a passage which extends from a first end positioned and structured to receive the flow of breathing gas from the gas flow generator to an opposite second end positioned on the lid and structured to expel the flow of breathing gas into the chamber, wherein a portion of the passage is defined by the coupling arrangement; and
an outlet positioned on the housing, the outlet being structured to convey the flow of breathing gas from the chamber out of the housing,
wherein the coupling arrangement comprises a generally cylindrical portion disposed about a rotational axis of the lid relative to the housing; and wherein the portion of the passage comprises a hollow defined in the cylindrical portion;
a delivery conduit having a first end coupled to the outlet of the apparatus and an opposite second end, the conduit being structured to convey the flow of breathing gas from the first end to the second end; and a patient interface device coupled to the second end of the conduit for providing the flow of treatment gas to the airway of the patient.

18. The system of claim 17, wherein the hollow extends from an inlet which is positioned to initially receive the flow of breathing gas entering the hollow;

and wherein the inlet is disposed on a face selected from the group consisting of an axial face of the cylindrical portion and a circumferential face of the cylindrical portion.

19. The system of claim 18, wherein, when the lid is disposed in the first position, the inlet is positioned to receive the flow of breathing gas; and wherein, when the lid is disposed in the second position, the inlet is positioned to not receive the flow of breathing gas.

20. The system of claim 17, wherein the cylindrical portion is fixedly coupled to the lid.

\* \* \* \* \*